US012102762B2

(12) United States Patent
Chou et al.

(10) Patent No.: US 12,102,762 B2
(45) Date of Patent: Oct. 1, 2024

(54) NASAL CANNULA DEVICE

(71) Applicant: FOXXMED LTD., Yilan County (TW)

(72) Inventors: Jeng-Yu Chou, Yilan County (TW); Wen-Hsien Liu, Yilan County (TW); Kuang-Ming Chiang, Yilan County (TW); Yung-Yang Shih, Yilan County (TW)

(73) Assignee: FOXXMED LTD., Yilan County (TW)

( * ) Notice: Subject to any disclaimer, the term of this patent is extended or adjusted under 35 U.S.C. 154(b) by 814 days.

(21) Appl. No.: 17/188,919

(22) Filed: Mar. 1, 2021

(65) Prior Publication Data

US 2021/0178100 A1   Jun. 17, 2021

Related U.S. Application Data

(63) Continuation-in-part of application No. 17/115,150, filed on Dec. 8, 2020, now Pat. No. 11,684,742, (Continued)

(51) Int. Cl.
*A61M 16/06* (2006.01)
*A61M 16/08* (2006.01)

(52) U.S. Cl.
CPC ..... *A61M 16/0672* (2014.02); *A61M 16/0683* (2013.01); *A61M 16/0816* (2013.01);
(Continued)

(58) Field of Classification Search
CPC .............. A61M 16/06; A61M 16/0666; A61M 16/0672; A61M 16/0683; A61M 16/0816; A61M 2205/0216
See application file for complete search history.

(56) References Cited

U.S. PATENT DOCUMENTS

2010/0192957 A1* 8/2010 Hobson ............. A61M 16/0672
                                                              128/207.18
2011/0067704 A1* 3/2011 Kooij ................ A61M 16/0858
                                                              128/207.18
(Continued)

*Primary Examiner* — Joseph D. Boecker
(74) *Attorney, Agent, or Firm* — NZ CARR LAW OFFICE (57) ABSTRACT

Disclosed herein are novel designs of a nasal cannula device suitable for supplying a flow of respiratory gas to a user during respiratory therapy. In one design, the nasal cannula device includes a cannula body, and a base. The cannula body has a front, top, and rear sides, in which the rear side is substantially longer than the front side and flattens out at both ends in the form of a wing, and a tab extending out from the lower end of the rear side. At least one nasal joint tube extends out from the top side of the cannula body, and a first connecting member is formed on the tab. The base includes, an opening formed on the top of the base; two through holes respectively formed on the left and right ends of the base; and a second connecting member formed on the bottom of the base. The first and second connecting members are configured to engage with each other thereby enclosing the base within a space collectively defined by the front, top, and rear sides, and the tab of the cannula body. In another design, the nasal cannula device includes a cannula body having a tubular body, in which one side of the tubular body is substantially longer than the rest of the tubular body and flattens out at both ends in the form of a wing, and a nasal joint tube extends out from the outer surface of the cannula body.

16 Claims, 11 Drawing Sheets

Related U.S. Application Data which is a continuation of application No. 16/038,124, filed on Jul. 17, 2018, now Pat. No. 10,905,840.

(52) U.S. Cl.
CPC . *A61M 16/0875* (2013.01); *A61M 2202/0208* (2013.01); *A61M 2205/0216* (2013.01); *A61M 2205/42* (2013.01)

(56) References Cited

U.S. PATENT DOCUMENTS

| | | | |
|---|---|---|---|
| 2014/0202466 A1* | 7/2014 | Ho | A61M 16/0666 128/206.24 |
| 2016/0030696 A1* | 2/2016 | Klenner | A61M 16/0066 128/207.18 |
| 2019/0240438 A1* | 8/2019 | Stenzler | A61M 16/0683 |
| 2020/0023153 A1* | 1/2020 | Chou | A61M 16/0816 |
| 2024/0091482 A1* | 3/2024 | Bazoberry | A61M 16/0078 |
| 2024/0157079 A1* | 5/2024 | Xu | A61M 16/0816 |

* cited by examiner

NASAL CANNULA DEVICE

CROSS-REFERENCE TO RELATED APPLICATION

This application is a continuation-in-part of U.S. application Ser. No. 17/115,150 filed Dec. 8, 2020, which is a continuation application of U.S. application Ser. No. 16/038,124 filed Jul. 17, 2018 and now issued as U.S. Pat. No. 10,905,840, each of which is incorporated herein by reference in its entirety.

BACKGROUND OF THE INVENTION

1. Field of the Invention

The present invention relates to two novel designs of a nasal cannula device, which is suitable for use in respiratory therapy for the delivery of a. stream of gas during respiratory therapy.

2. Description of Related Art

A nasal cannula device, such as the one taught in US 2020/0023153A1, is commonly used in respiratory therapy for the supply of a respiratory gas to patients in need of assisted respiration. During operation, nasal joint tubes of the nasal cannula device are inserted into the nostrils of the patient, so that supplemental oxygen and/or humidified therapeutic gas may be delivered to the patient's respiratory tract. However, the nasal joint tubes of the nasal cannula device tend to bend and deform when compressed, thereby results in inadvertently closing the air conduit in the nasal, joint tube and jeopardizing the patient's health.

In view of the problem presently exists in the related art, there is a need of an improved design of the nasal cannula device, which would prevent the air conduit in the nasal joint tube from being inadvertently closed, and ensure continued supply of a respiratory gas to its recipient.

SUMMARY

In accordance with the first aspect of the present disclosure, there is provided a nasal cannula device suitable for supplying a flow of respiratory gas to a user. The nasal cannula device includes at least a cannula body, and a base, wherein, the cannula body has a front, top, and rear sides, in which the rear side is substantially longer than the front side and flattens out at both ends in the form of a wing, and the cannula body comprises, a tab extending out from the lower end of the rear surface;

a nasal joint tube extending out from the top surface of the cannula body, and a first connecting member formed on the tab; wherein, the front, top, and rear sides, and the tab collectively defines a space for accommodating the base therein; and the base comprises, an opening formed on the top of the base;

two through holes respectively formed on the left and right ends of the base; and a second connecting member formed on the bottom of the base; wherein, the first and second connecting members are configured to engage with each other thereby enclosing the base within the space collectively defined by the front, top, and rear sides, and the tab of the cannula body.

According to preferred embodiments of the present disclosure, the first connecting member may be an aperture formed on the tab, while the second connecting member may be a protrusion formed on the bottom outer surface of the base, or vice versa.

Additionally, or alternatively, the top surface of the cannula body may further include a recess area, in which the nasal joint tube extends therefrom.

Additionally, or alternatively, the nasal joint tube may further include a junction ring disposed around the foot of the nasal joint tube, and the junction ring has a constant height or a height that varies along the circumference of the nasal joint tube.

Additionally, or alternatively, the nasal joint tube further includes a recessed annular section recessed from the outer surface or the inner surface of the nasal joint tube.

Additionally, or alternatively, the nasal joint tube further includes a ribbed section having one or more ribs disposed longitudinally around the outer surface or the inner surface of the nasal joint tube.

Additionally, or alternatively, the nasal joint tube may further include a protruding annular section protruded from the outer surface or the inner surface of the nasal joint tube.

Additionally, or alternatively, at least one part of the nasal joint tube is made from a relatively less rigid material as compared with that of the rest of the nasal joint tube.

Additionally, or alternatively, the nasal joint tube may further include an aperture formed thereon.

Additionally, or alternatively, the rear side of the cannula body further comprises two blocking tabs respectively formed at each ends of the wing to help secure the head gear in place.

Additionally, or alternatively, the cannula device further includes a head gear having two supporters, which are coupled to the left and right ends of the base, respectively.

In accordance with the second aspect of the present disclosure, there is provided a nasal cannula device suitable for supplying a flow of respiratory gas to a user. The nasal cannula device includes, a cannula body having a tubular body, in which one side of the tubular body is substantially longer than the rest of the tubular body and flattens out at both ends in the form of a wing; and a nasal joint tube extended out from the outer surface of the tubular body.

Additionally, or alternatively, the tubular body may further include a recessed area on its outer surface, in which the nasal joint tube extends out from the recessed area.

Additionally, or alternatively, the nasal joint tube may further include a junction ring disposed around the foot of the nasal joint tube, and the junction ring has a constant height or a height that varies along the circumference of the nasal joint tube.

Additionally, or alternatively, the nasal joint tube may further include a recessed annular section recessed from the outer surface or the inner surface of the nasal joint tube.

Additionally, or alternatively, the nasal joint tube may further include a ribbed section having one or more ribs disposed longitudinally around the outer surface or the inner surface of the nasal joint tube.

Additionally, or alternatively, the nasal joint tube may further include a protruding annular section protruded from the outer surface or the inner surface of the nasal joint tube.

Additionally, or alternatively, at least one part of the nasal joint tube is made from a relatively less rigid material as compared with that of the rest of the nasal joint tube.

Additionally, or alternatively, the nasal joint tube may further include an aperture formed thereon.

Additionally, or alternatively, the nasal cannula device may further include a head gear having two supporters, which are coupled to the left and right ends of the cannula body, respectively.

Additionally, or alternatively, the nasal cannula device may further include two adapters for coupling the two supporters to the left or right ends of the cannula body, respectively.

Additionally, or alternatively, the side of the tubular body that is substantially longer further comprises two blocking tabs respectively formed at each ends of the wing to help secure the head gear in place.

BRIEF DESCRIPTION OF THE DRAWINGS

The disclosure will become more fully understood from the detailed description and the drawings given herein below for illustration only, and thus does not limit the disclosure wherein.

DETAILED DESCRIPTION

Detailed descriptions and technical contents of the present disclosure are illustrated below in conjunction with the accompanying drawings. However, it is to be understood that the descriptions and the accompanying drawings disclosed herein are merely illustrative and exemplary and not intended to limit the scope of the present disclosure.

1. Respiratory System

Figure 1:
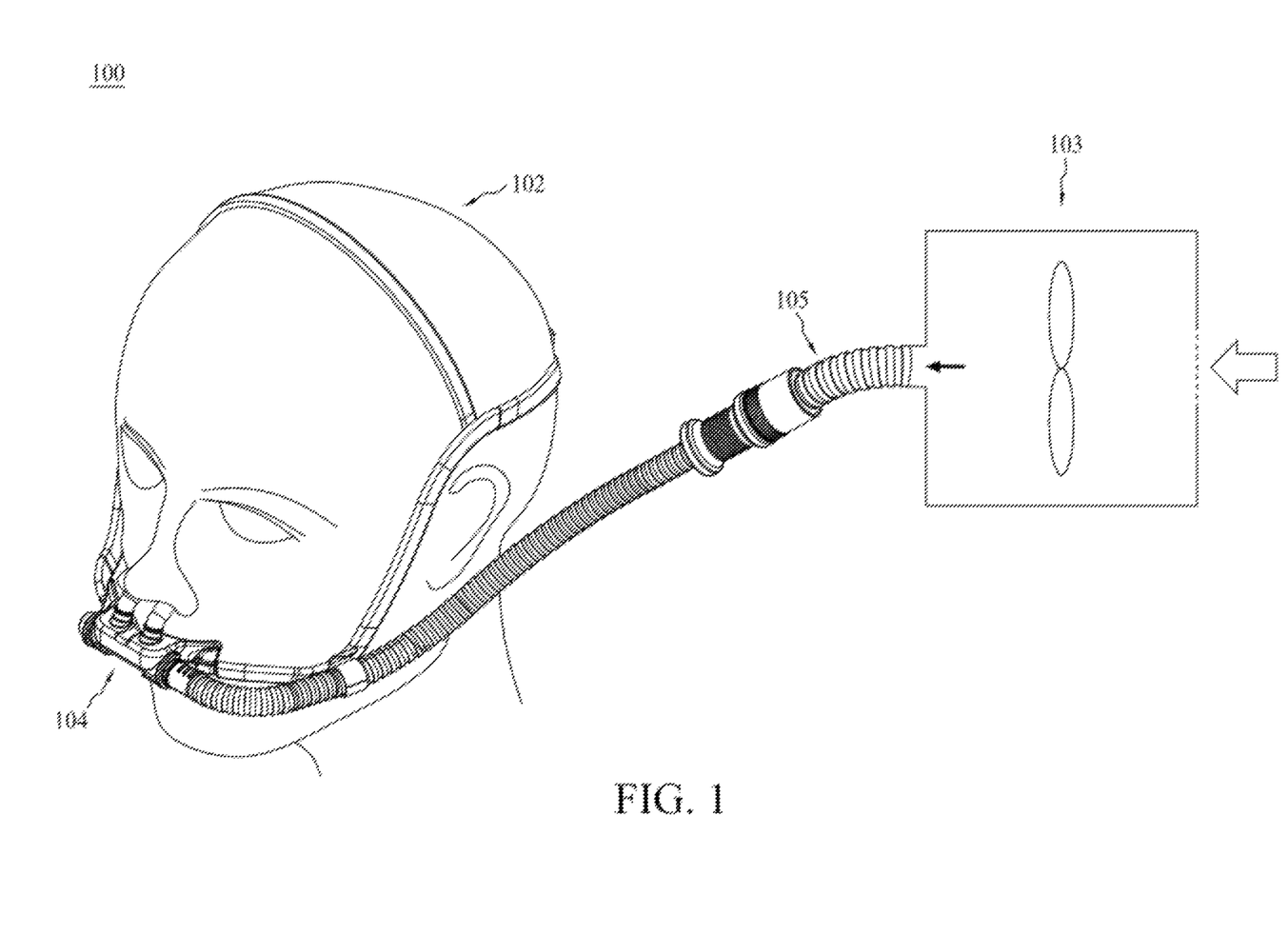
FIG. 1 is a schematic diagram of a conventional respiratory system for providing a stream of respiratory gas to a user during respiratory therapy.

FIG. 1 is a schematic diagram of a respiratory system 100 for providing a stream of respiratory gas to a user 102 during respiratory therapy. The respiratory system 100 typically includes at least, a gas supply unit 103, a nasal cannula device 104, and a supply conduit 105, in which the supply conduit 105 is connected to the gas supply unit 103 at one end and to the nasal cannula device 104 at the other end. When in use, the gas supply unit 103 may provide a stream of gas (e.g., oxygen or air) at a pre-determined pressure, flow rate and/or humidity to the user 102 with the aid of the nasal cannula device 104, such as the one that will be described below.

2. Nasal Cannula Device

Figure 2A:
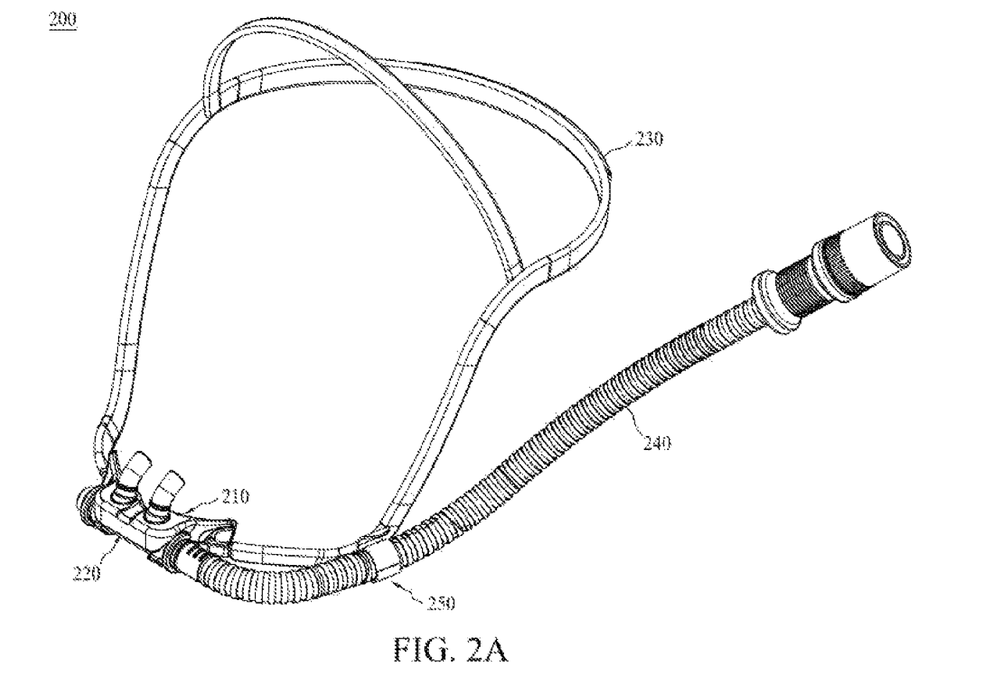
FIG. 2A is a perspective view of a nasal cannula device suitable for use with the respiratory system of FIG. 1. in accordance with one embodiment of the present disclosure.

FIG. 2A is a schematic drawing of the present nasal cannula device 200 suitable for use with a respiratory system (e.g., the one depicted in FIG. 1) for providing a stream of respiratory gas to a user during respiratory therapy. The nasal cannula device 200 includes at least, a cannula body 210, a base 220, a head gear 230; and optionally, an air tube 240, and a clamp 250. The air tube 240 is coupled to one end of the base 220, and the clamp 250 helps secure the air tube 240 to the head gear 230, and at the same time, help balance the weight of the device 200 when it is worn on the user's head. In operation, when one end of the base 220 is connected to the air tube 240, then the other end of the base 220 is closed with a plug. Note that the plug is not visible from FIG. 2A.

Figure 2B:
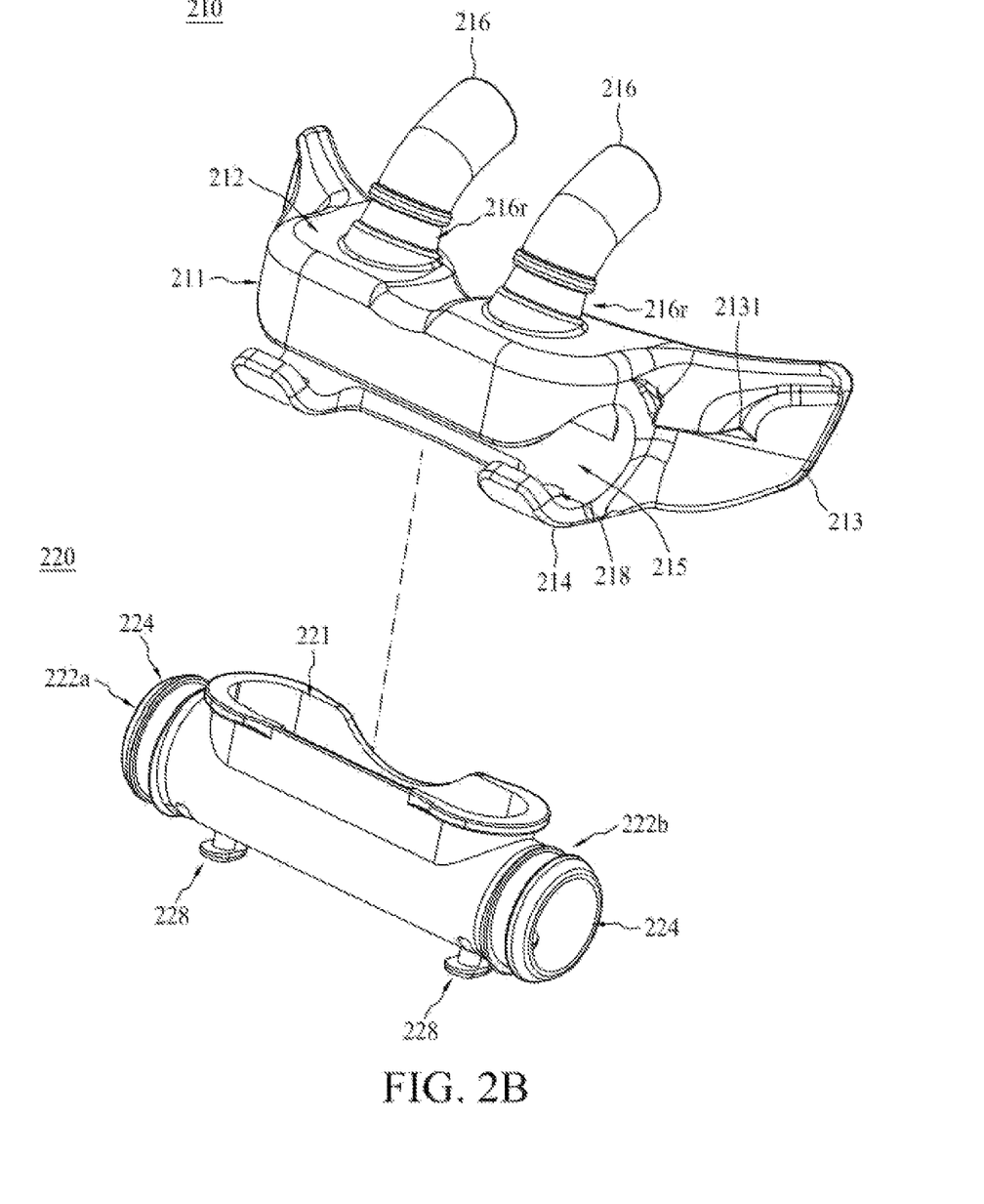
FIG. 2B are schematic diagrams of a cannula body and a base of the nasal cannula device of FIG. 2A.
Figure 2C:
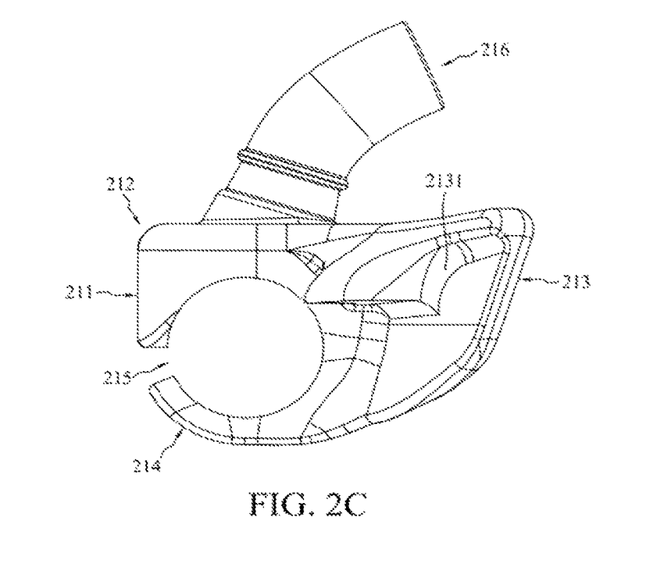
FIG. 2C is a side view of the cannula body of FIG. 2B.

Referring to FIG. 2B, which depicts the cannula body 210 and the base 220. The cannula body 210 has in its structure, a front side 211, a top side 212, a rear side 213, and two tabs 214 respectively extending from the lower end of the rear side 213. The rear side 213 is substantially longer than the front side 211 and flattens out at both ends in the form of a wing. The front, the top, the rear sides 211, 212, 213, and the two tabs 214 collectively define a space 215 for accommodating the base 220 therein when the cannula body 210 and the base 220 are assembled to form the device 200. Referring to FIG. 2C, which is a side view of the cannula body 210, in which the space 215 for accommodating the base 220 is revealed. Additionally, two nasal joint tubes 216 are independently formed and extended out from the top side 212 of the cannula body 210 for inserting into the nostrils of a user. Further, each tab 214 has an aperture 218 formed thereon for subsequent coupling with the base 220. Note that in this embodiment, each nasal joint tube 216 has a recessed annular section 216r recessed from its outer surface, however, in alternative embodiments, the recessed annular section 216r may be recessed from the inner surface of the tube 216, which will be described in FIG. 4.

Figure 3A:
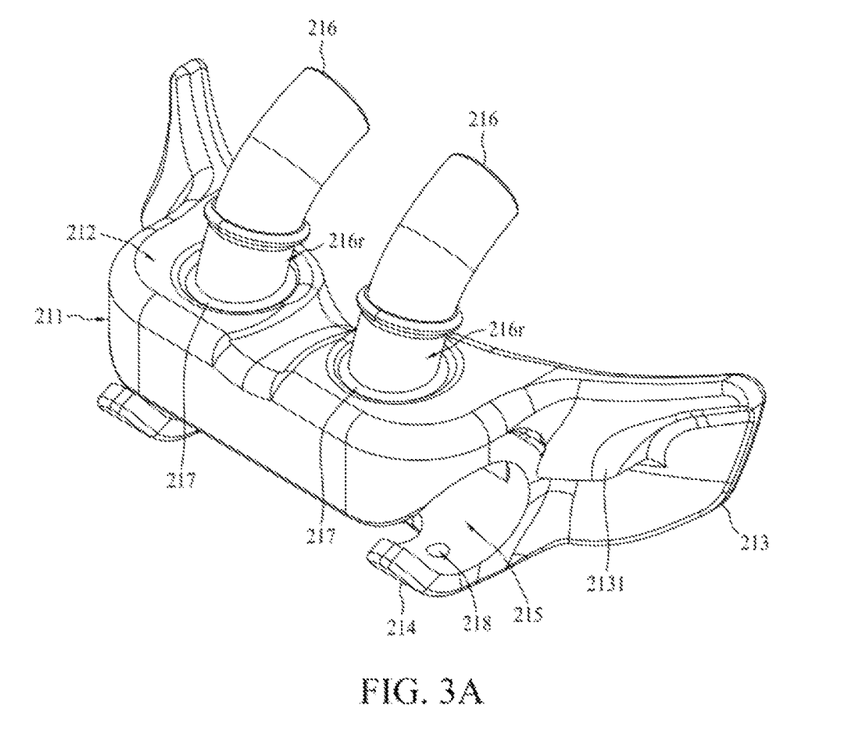
FIG. 3A is the perspective view of the cannula body of FIG. 2B in accordance with one embodiment of the present disclosure.
Figure 3B:
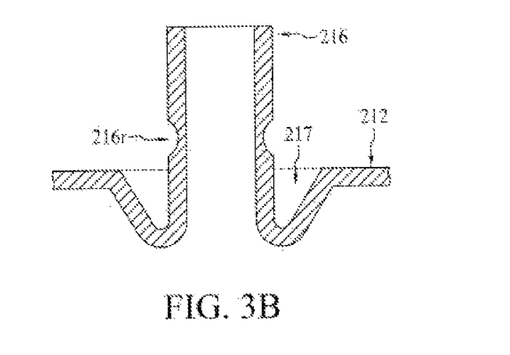
FIG. 3B is the cross-sectional view of the nasal joint tube of FIG. 3A.
Figure 3C:
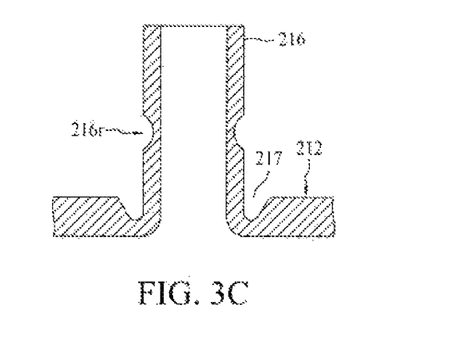
FIG. 3C is the cross-sectional view of another nasal, joint tube.

Additionally, or alternatively, the top side 212 of the cannula body 210 may further include two recessed areas 217, in which the two nasal joint tube 216 are respectively formed and extended thereout (FIG. 3A). In some embodiments, the nasal joint tube 216 has the same thickness as that of the top side 212 of the cannula body 210 (FIG. 3B). In other embodiments, the nasal joint tube 216 has a thickness that is smaller than that of the top side 212 of the cannula body 210 (FIG. 3C). Additionally, or alternatively, the rear side 213 of the cannula body 210, which is in the form of a wing, may further include two blocking tabs 2131 respectively formed at each ends of the wing to help secure the head gear 230 in place (i.e., from moving) (FIGS. 2A, 2B, 2C and 3A).

Referring to FIG. 2B again, the base 220 of the cannula body 210 comprises in its structure, an opening 221 formed on the top of the base 220, two through holes 224 respectively formed at the left and right ends 222a, 222b of the base 220, and two protrusions 228 independently formed and extended from the bottom outer surface of the base 220.

When in use, the cannula body 210 and the base 220 are manually assembled via engaging the two protrusion 228 of the base 220 with the two apertures 218 of the tabs 214 thereby securely enclosing the base 220 within the space 215 collectively defined by the front, the top, the rear sides 211, 212, 213, and the two tabs 214 of the cannula body 210. Additionally, or alternatively, each tab 214 of the cannula body 210 may have a protrusion protruding out from its surface, while the bottom surface of the base 220 may have two corresponding apertures formed thereon, so that the two protrusions of the tabs 214 may engage with the two apertures of the base 220 thereby securely enclosing the base 220 within the space of the cannula body 210. Note that the engagement of the two protrusion 228 and the two apertures 218 also places the opening 221 of the base 220 right underneath the two nasal joint tubes 216 thereby forms an air conduit allowing the stream of gas (e.g., supplied from the gas supply unit 103 via the supply conduit 105) to pass the nasal cannula device 200 and enters the user's nostrils.

The cannula body 210 and the base 220 may be made of same or different material. Examples of the material suitable for making the cannula body 210 and the base 220 include, but are not limited to, silicone, polypropylene (PP), polyethylene (PE), polycarbonate (PC), polyvinylchloride (PVC), polycaprolactone (PCL), acrylonitrile butadiene styrene (ABS), polysulfone (PSU), polycyclohexylenedimethylene terephthalate glycol (PCTG) and the like. According to preferred embodiments of the present disclosure, the cannula. body 210 is made of silicone, while the base 220 is made of PC.

2.1 The Nasal Joint Tube

Figure 4:
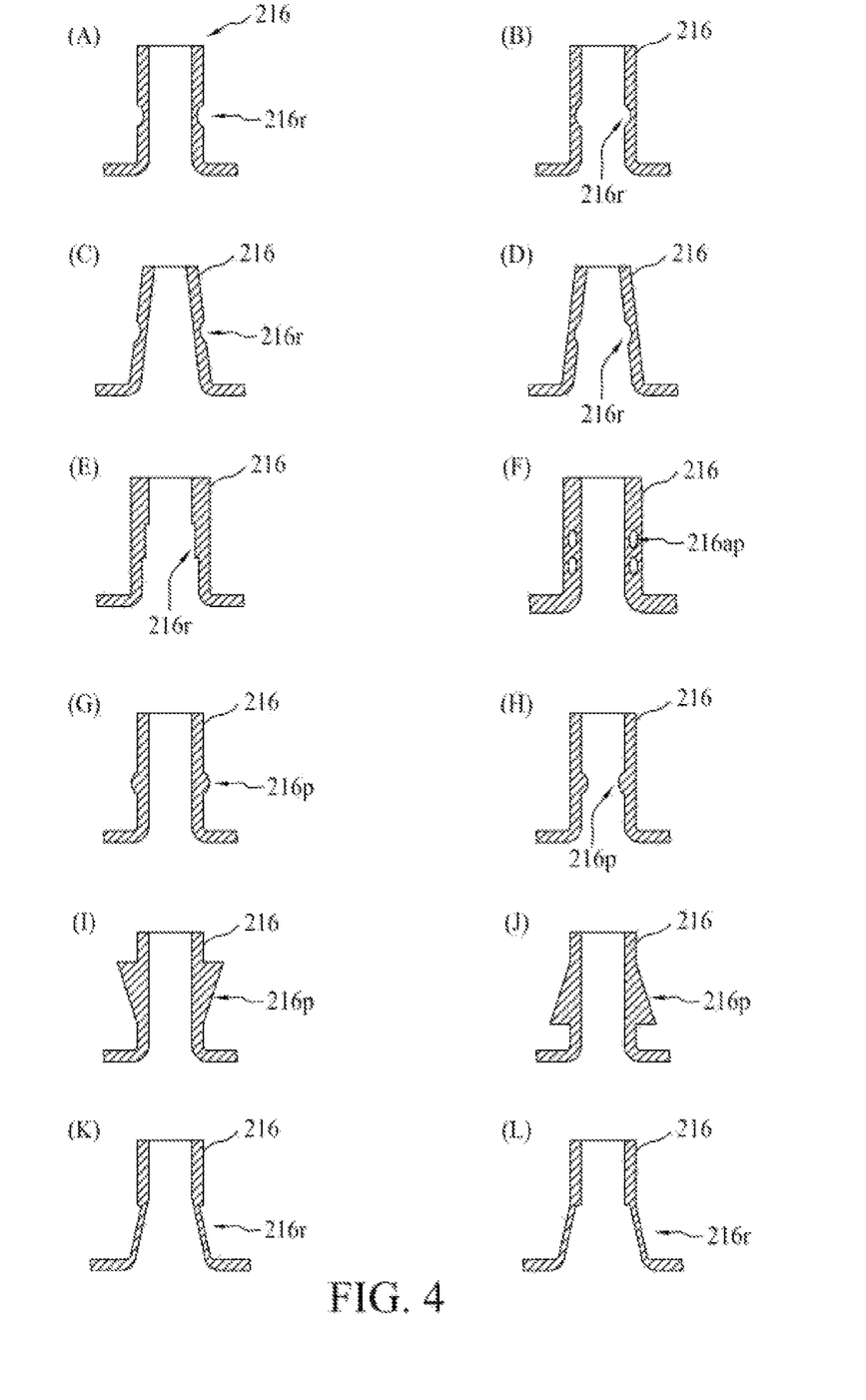
FIG. 4 are cross-sectional views of various forms of a nasal joint tube in accordance with one embodiment of the present disclosure.

References are now made to FIGS. 4 to 6, which are schematic drawings of various forms of the present nasal joint tube, such as the one depicted in FIG. 2 or 3. In general, each nasal joint tube suitable for use in the present invention may have an inner diameter that remains constant throughout its entire length (FIG. 4, (A), (F), (G), (I) and (J)), or may be varied from one part to another (FIG. 4, (B) to (E), (H), (K) and (L)). In some embodiments, the nasal joint tube has an inner diameter that decreases gradually from its foot towards the top (FIG. 4, (C) and (D)). In other embodiments, the nasal joint tube has an inner diameter that decreases step-wisely (FIG. 4, (E)). in further embodiments, at least one part of the tube has an inner diameter that remains constant, while the other part of the tube has an inner diameter that varies gradually (FIG. 4, (B), (D), (K), and (L)).

Further, at least one section of the nasal joint tube is made less rigid or more rigid than that of the rest of the tube. In either situation, the section chosen to be modified (i.e., the section being made less or more rigid as compared to other parts of the tube) is pre-determined, preferably, modification is made to the section of the tube close to its foot.

(i) Recessed and Protruded Annular Sections

To make certain section of the nasal joint tube 216 less rigid than the rest of the tube, the nasal joint tube may further include a recessed annular section 216r, which may be recessed from the outer surface or the inner surface of the nasal joint tube 216 (FIG. 4, (A) to (E), and (K) to (L)). In certain embodiments, the recessed annular section 216r is recessed in rounded form in cross section from the outer or inner surfaces of the tube 216 (FIG. 4, (A) to (D), and (K) to (L)). Preferably, the inner diameter of the nasal joint tube 216 in the recessed annular section 216r decreases gradually from its foot towards the top, while that of the other part of the nasal joint tube 216 remains constant (FIG. 4, (K) and (L)). In other embodiments, the recessed annular section 216r is recessed trapezoidally in cross section in two steps from the inner surface of the tube 216 (FIG. 4, (E)). Additionally, Of alternatively, instead of having a recessed annular section, certain section of the nasal joint tube (e.g., from the foot above certain height/length of the tube) may be made from a less rigid material or soft material (e.g., silicone), while the other part of the nasal joint tube is made from a more rigid material (e.g., PVC, PE, PCL, and etc). Alternatively, the tube may be made from same type of material having different mechanical strength (e.g., hardness), for example, certain section is made from silicon with a shore hardness of 50A, while the other part of the tube is made from silicon with a shore hardness of 30A. Still alternatively or optionally, certain section of the nasal joint tube may be made less rigid by creating one or more apertures thereon to weaken the mechanical strength of the tube (FIG. 4, (F)).

To make one section of the nasal joint tube more rigid than the rest of the tube, the nasal joint tube 216 may further include a protruding annular section 216p, which may be protruded from the outer surface or the inner surface of the nasal joint tube 216 (FIG. 4, (G) to (J)). In certain embodiments, the protruded annular section 216p protrudes in rounded form in cross section from the outer or inner surfaces of the tube 216 (FIG. 4, (G) and (H)). In other embodiments, the protruding annular section 216p protrudes perpendicularly out from the outer surfaces of the tube 216, then tapers up or down along the outer surface until it rejoins the tube body, thereby having a triangular form in cross section (FIG. 4, (I) and (J)).

(II) Ribbed Section

Additionally, or alternatively, a ribbed section 216s, which comprises a plurality of parallel ribs 219, may be included in each nasal joint tube (FIG. 5).

Figure 5A:
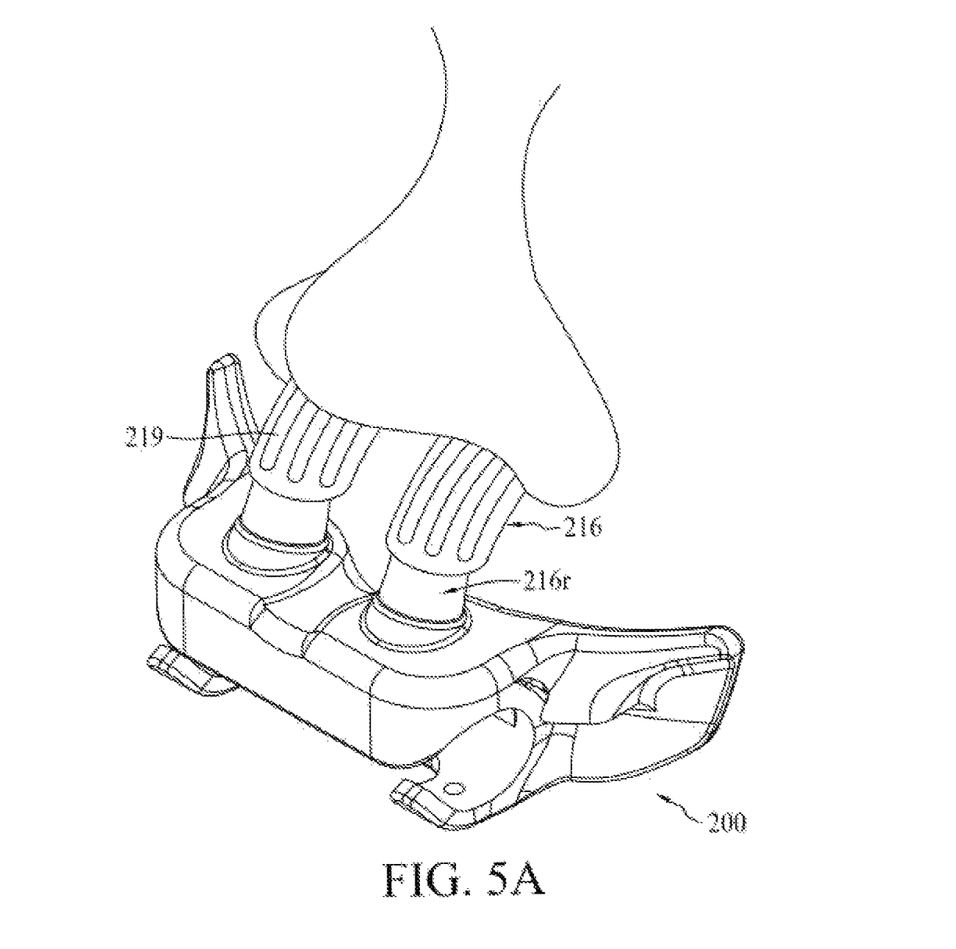
FIG. 5A a perspective view of a nasal joint tube having a ribbed section in accordance with one embodiment of the present disclosure.
Figure 5B:
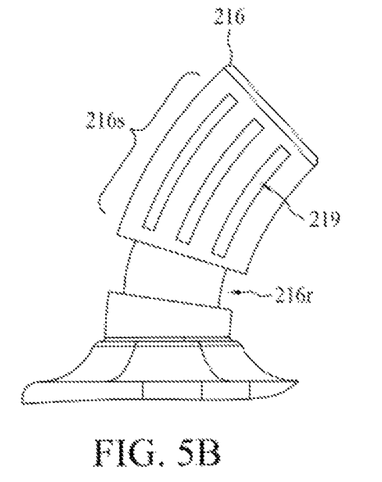
FIG. 5B is a sideview of the nasal joint tube of FIG. 5A.
Figure 5C:
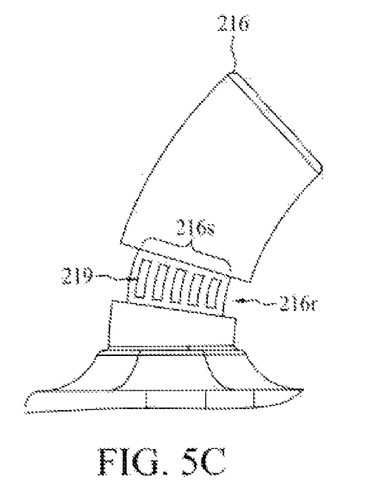
FIG 5C is a side view of a nasal joint tube having a ribbed section the annular recessed area in accordance with another embodiment of the present disclosure.
Figure 5D:
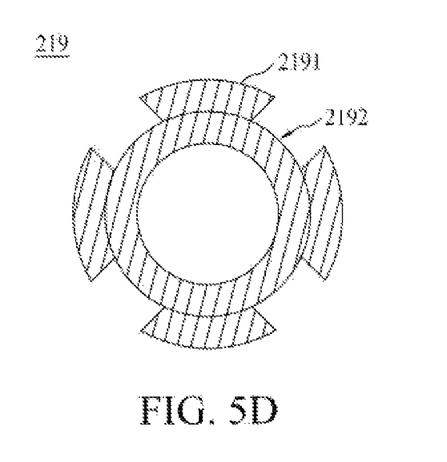
FIG. 5D is a cross sectional view of the ribbed section of the nasal joint tube of FIG. 5A.
Figure 5E:
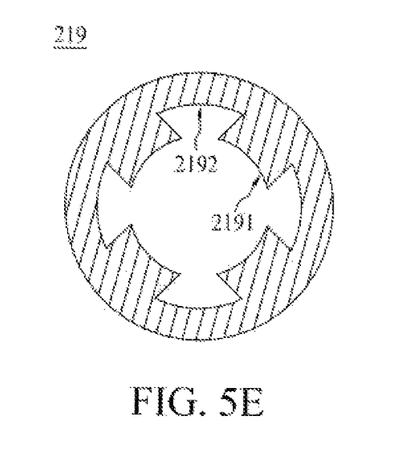
FIG. 5E is a cross sectional view of the ribbed section of another nasal joint tube.

In one preferred form, the ribbed section 216s extends around the circumferential perimeter of the nasal joint tube 216, and above the recessed annular section 216r (FIGS. 5A and 5B). Alternatively, the ribbed section 216s may also extend the full length of the tube. In another preferred form, the ribbed section 216s may be disposed right within the recessed annular section 216r (FIG. 5C), The ribbed section 216s is formed from adjacent parallel ribs 219, with the ribs 219 being parallel to the longitudinal axis of the tube 216. Each rib 219 is formed in the tube 216 by having thick-walled portions 2191 parallel to the longitudinal axis of the tube 216. The thick-walled portions 2191 are separated from adjacent thick-wailed portions 2191 by intervening thin-walled portions 2192, the thin-walled portions 2192 being parallel to the longitudinal axis of the tube 216 (i.e., around the circumferential perimeter of the tube). The thick-wailed portions 2191 alternate with the thin-walled portions 2192, thus each rib 219 is made up of one thick-walled portion 2191 with a thin-walled portion on either side (FIGS. 5D and 5E), The thick-walled portions 2191 and the thin-wailed portions 2192 may be formed substantially circular, arc, square, rectangular, triangular or trapezoid in cross section, or may be in any desirable shape. Alternatively, the ribbed section of the tube may be formed with the outer surface of the ribbed section being smooth, and the circular, arc, square, rectangular, triangular or trapezoid-wave type ribbed profile in the inner surface of the ribbed section. Alternatively, a center line of the thick-walled portions 2191 may be aligned or offset so that the circular, arc, square, rectangular, triangular or trapezoid-wave type ribbed profile is in both the inner and outer surfaces of the ribbed section 216s.

(iii) Junction Ring

Figure 6A:
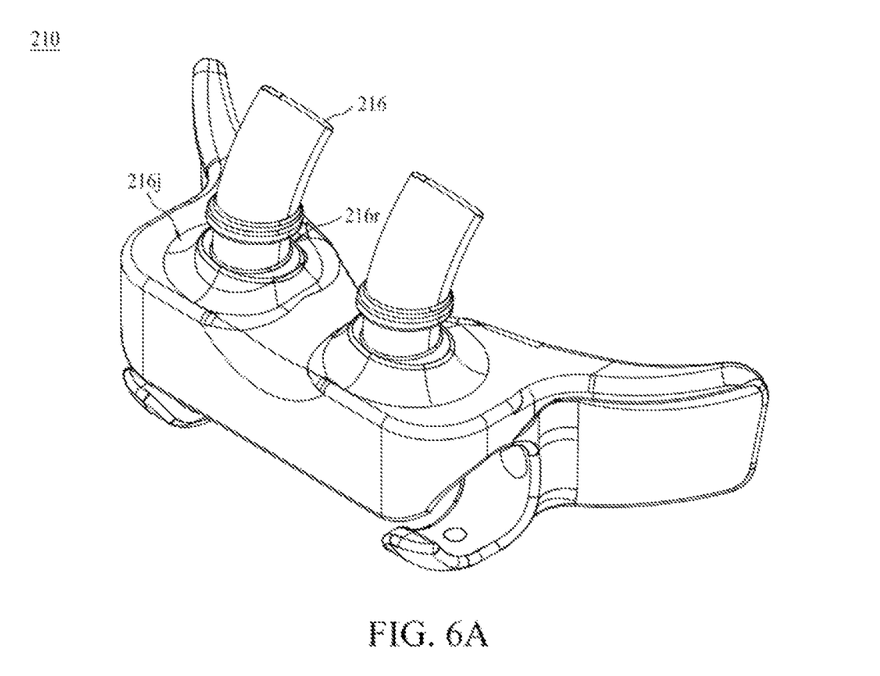
FIG. 6A is a perspective view of a cannula body, in which the nasal joint tube further includes a junction ring, at its foot.
Figure 6B:
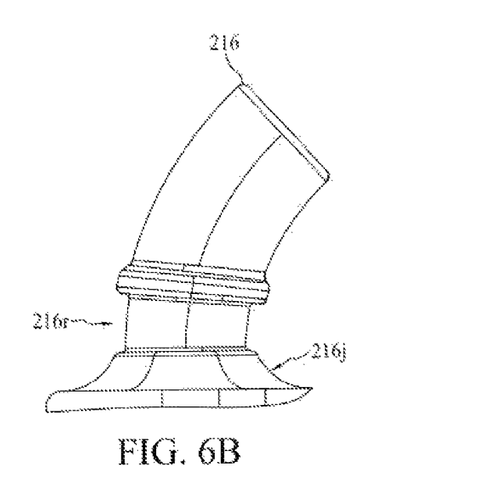
FIG. 6B is a side view of the nasal joint tube of FIG. 6A.
Figure 6C:
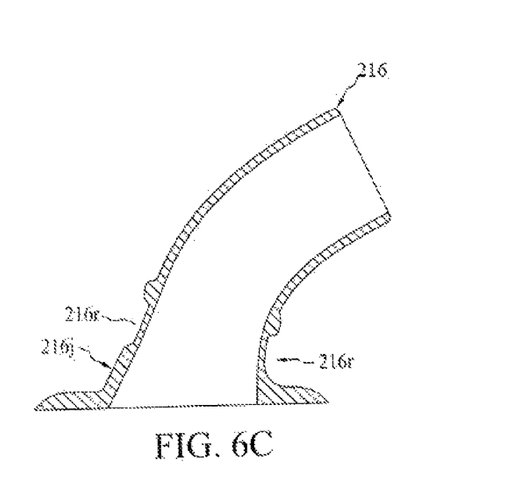
FIG. 6C is a cross sectional view of another nasal joint tube having a junction ring, with its height varied along the circumference of the nasal joint tube.

Additionally, or alternatively, the nasal joint tube 216, such as the one depicted in FIGS. 2B, 5 or 6, may further include a junction ring 216j disposed around the foot of the nasal joint tube 216 (FIG. 6A). In some embodiment, the junction ring 216j has a constant height (FIG. 6B). In other embodiments, the height of the junction ring 216j varies along its top circumference or the circumference of the nasal joint tube 216 (FIG. 6C).

2.2 The Head Gear

Figure 7:
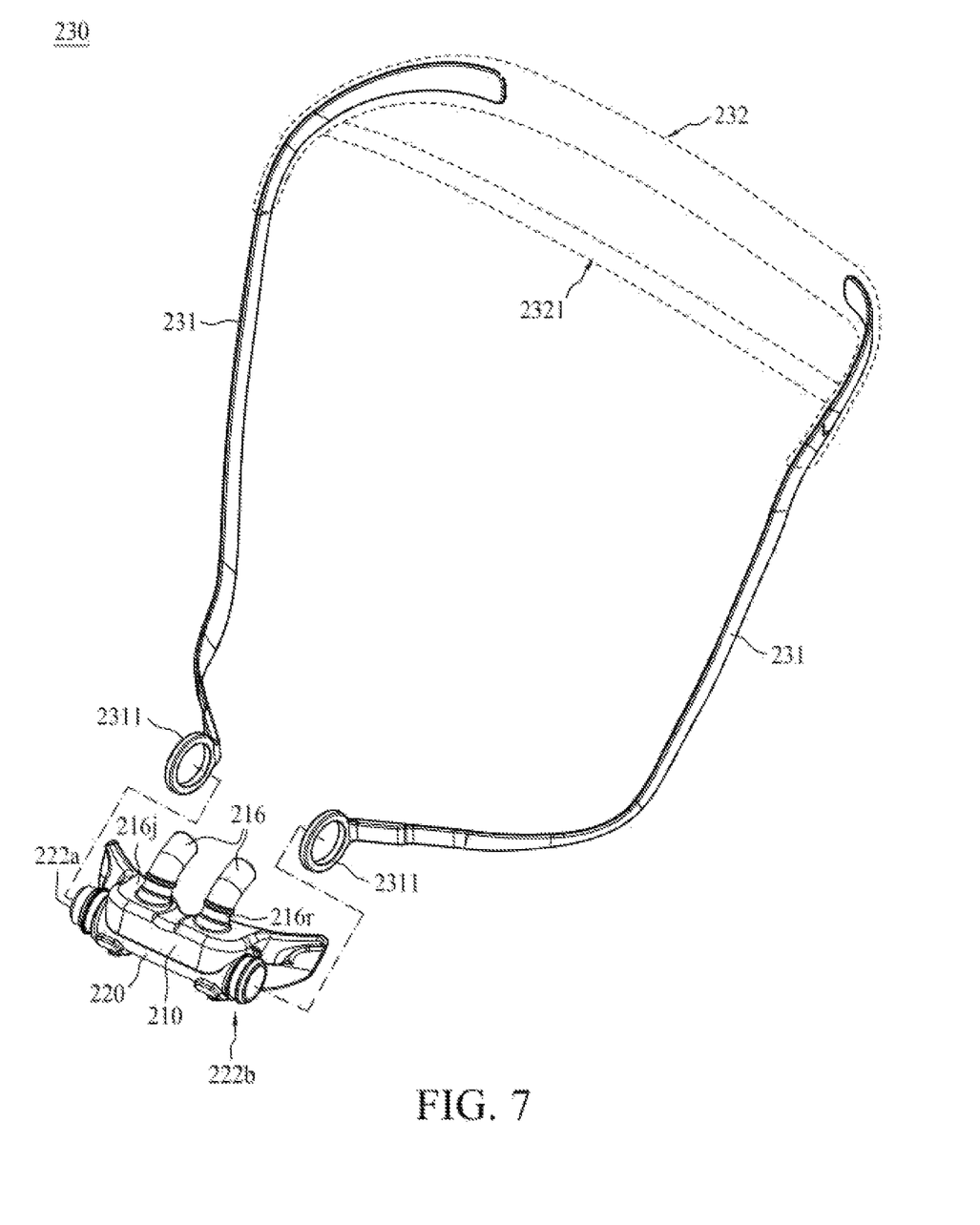
FIG. 7 illustrates the assembly of a head gear with the present nasal cannula device.

Referring to FIG. 7, the nasal cannula device 200 also includes a head gear 230 coupled to the left and right ends 222a, 222b of the base 220. The head gear 230 includes at least, two flexible supporters 231 and an elastic fabric cover 232. Each flexible over-ear supporter 231 has two ends, in which one end has a fastener 2311 extended thereout for coupling to the left or right ends 222a, 222b of the base 220, while the other end of the over-ear supporter 231 is received in the elastic fabric cover 232. The fastener 2311 may be in the shape of a letter "C", "D", "O" or "U." In the embodiment depicted in FIG. 7, each fastener 2311 has the shape of the letter "O", capable of encircling the left or right ends 222a, 222b of the flexible supporter 231 therein. Note that the shape of the fastener 2311 is not limited to the indicated shapes, as long as it may securely couple the flexible supporter 231 to the base 220.

Returning to the elastic fabric cover 232, which is substantially in the form of a tube and has two open ends for receiving respective ends of the two supporters 231. Additionally the elastic fabric cover 232 further includes an over-head strap 2321, which help securing the head gear 230 on the user's head and stabilizing the seal created between the nasal joint tubes 216 and the user's nasal cavity, which in turn prevents inadvertent detachment of the nasal joint tubes 216 from the nasal cavity when the device 200 is in use.

3. Alternative Form of the Nasal Cannula Device

In the embodiment described in Section 2 of this paper, the nasal cannula device 200 comprises in its structure, at least a cannula body 210 and a base 220. The cannula device in this alternative embodiment differs from that in Section 2 in that it does not require the presence of a base (e.g., the base 200 as described in FIGS. 2 to 7), thereby rendering the cannula device in this alternative embodiment more compact in structure, and lighter in weight, thus is more comfortable to wear when in use.

Figure 8A:
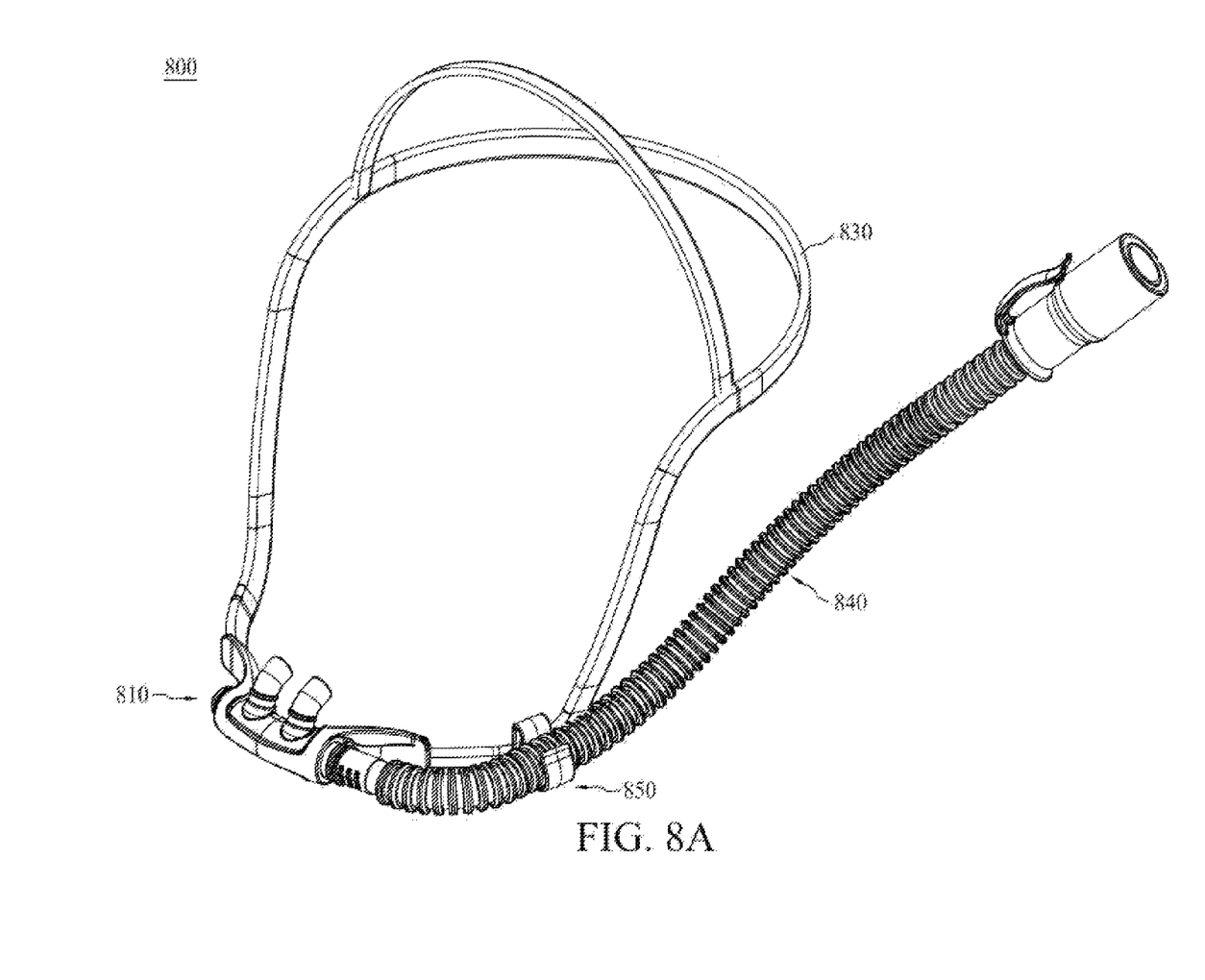
FIG. 8A is a perspective view of a cannula device in accordance with an alternative embodiment of the present disclosure.

Referring to FIG. 8, in which panel (A) is a perspective view of the cannula device 800 of this embodiment. The cannula device 800 includes, at least, a cannula body 810, a head gear 830; and optionally, an air tube 840, and a clamp 850. Note that in this embodiment, the air tube 840 is coupled to one end of cannula body 810, preferably through an adapter (not visible from FIG. 8), which will be described below. Like the function of clamp 250 described above, the clamp 850 helps secure the air tube 840 to the head gear 830, and at the same time, help balance the weight of the device 800 when it is worn on the user's head.

Figure 8B:
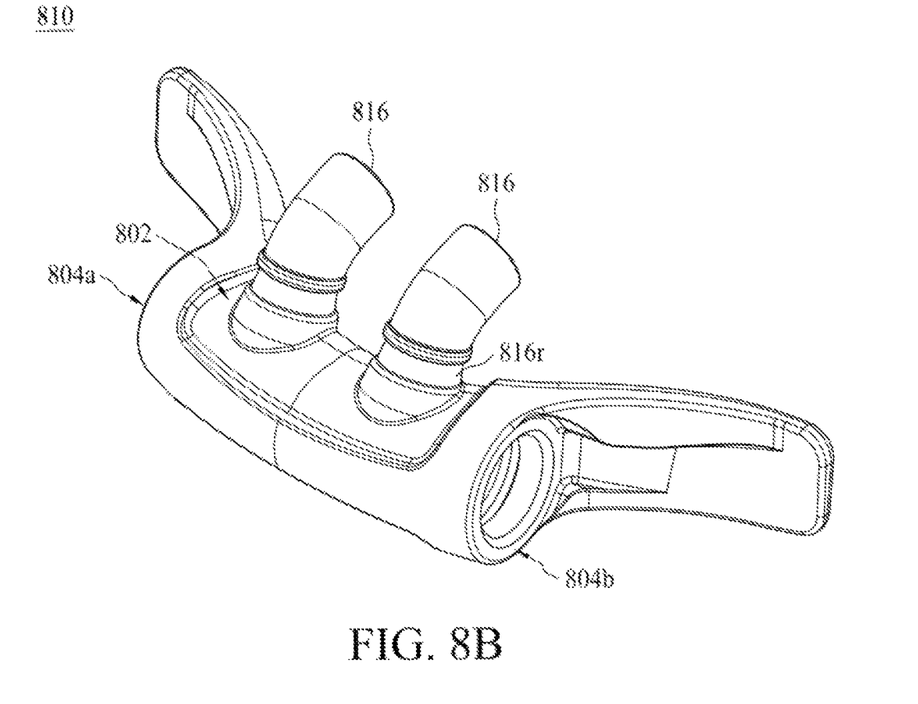
FIG. 8B is a front view of the cannula body of the device in FIG. 8A.

Turning to the cannula body 810, it has a tube-like structure with one side of the tube body being substantially longer than the other side in length and flattens out at both ends in the form of a wing (FIG. 8, (B)). The cannula body 810 comprises in its structure, a tubular body 802; and two nasal joint tubes 816, which independently extends out from the outer surface of the tubular body 802. The tubular body 802 has a hollow space 815 inside; and two open ends 804a, 804b, in which either ends 804a, 804b may be connected to the air tube 840. In operation, one end 804a, 804b of the tubular body 802 is connected to the air tube 840, while the other end 804a, 804b is dosed with a plug (not depicted). Additionally, or alternatively, an adapter (not depicted) may be used to connect the air tube 840 with either ends 804a, 804b of the tubular body 802, and the head gear 830 to the tubular body 802 as well. When the cannula body 810 is connected to the air tube 840, the hollow space 815 may serve as an air conduit allowing the stream of gas (e.g., supplied from the gas supply unit 103 via the supply conduit 105 depicted in FIG. 1) to pass the cannula body 800 and enters the user's nostrils. Additionally, or alternatively, the side of the annular body 810 that is substantially longer further comprises two blocking tabs respectively formed at each ends of the wing to help secure the head gear in place.

Figure 8C:
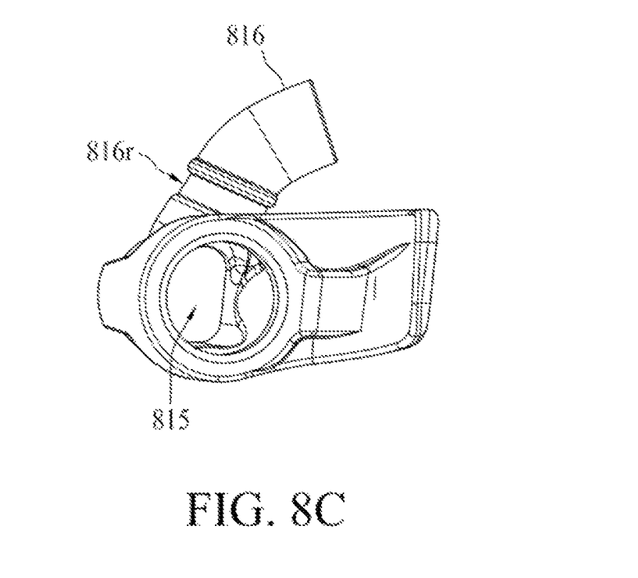
FIG. 8C is a side view of the cannula body in FIG. 8B.

The nasal joint tube 816 in this embodiment may be same as that described above in Sections 2.1, thus is not repeated here for the sake of brevity. As to the head gear 830, its components are substantially same as those described in Section 2.2, except in this embodiment, during assembling, the fastener of one of the two supporters may be coupled to a first adapter, then to a plug, which is used to close the end of the tubular body 802 not connected to the air tube 840; while the fastener of the other over-ear supporter may be coupled to a second adapter, in which one end of the second adapter is inserted into another open end of the tubular body 802, while the other end of the second adapter is connected to the air tube 840, thereby completes the assembling of the cannula device of this embodiment.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A nasal cannula device for supplying a flow of respiratory gas to a user comprising a cannula body and a base, wherein, the cannula body has front, top, and rear sides, in which
the cannula body flattens out at both lateral ends in the form of a wing, and the cannula body comprises,
a tab extending out from a lower end of the rear side;
a nasal joint tube extending out from a top side of the cannula body, and
a first connecting member formed on the tab;
wherein,
the front, top, and rear sides, and the tab collectively define a space for accommodating the base therein; and
the base comprises,
an opening formed on a top of the base;
two through holes respectively formed on left and right ends of the base; and a second connecting member formed on a bottom of the base;

wherein, the first and second connecting members are configured to engage with each other thereby enclosing the base within the space collectively defined by the front, top, and rear sides, and the tab of the cannula body.

2. The nasal cannula device of claim 1, wherein the first connecting member is an aperture formed on the tab, and the second connecting member is a protrusion formed on the bottom outer surface of the base, or vice versa.

3. The nasal cannula device of claim 2, wherein the top side of the cannula body further comprises a recess area, in which the nasal joint tube extends therefrom.

4. The nasal cannula device of claim 2, wherein the nasal joint tube further comprises a junction ring disposed around a foot of the nasal joint tube, and the junction ring has a constant height or a height that varies along a circumference of the nasal joint tube.

5. The nasal cannula device of claim 4, wherein the nasal joint tube further comprises a recessed annular section recessed from an outer surface or an inner surface of the nasal joint tube.

6. The nasal cannula device of claim 4, wherein the nasal joint tube further comprises a ribbed section having one or more ribs disposed longitudinally around an outer surface or an inner surface of the nasal joint tube.

7. The nasal cannula device of claim 4, wherein the nasal joint tube further comprises a protruding annular section protruded from an outer surface or an inner surface of the nasal joint tube.

8. The nasal cannula device of claim 4, wherein at least one part of the nasal joint tube is made from a relatively less rigid material as compared with that of the rest of the nasal joint tube.

9. The nasal cannula device of claim 4, wherein the nasal joint tube further comprises an aperture formed thereon.

10. The nasal cannula device of claim 2, wherein the nasal joint tube further comprises a recessed annular section recessed from an outer surface or an inner surface of the nasal joint tube.

11. The nasal cannula device of claim 10, wherein the nasal joint tube further comprises a ribbed section having one or more ribs disposed longitudinally around the outer surface or the inner surface of the nasal joint tube.

12. The nasal cannula device of claim 2, wherein the nasal joint tube further comprises a protruding annular section protruded from an outer surface or an inner surface of the nasal joint tube.

13. The nasal cannula device of claim 2, wherein at least one part of the nasal joint tube is made from a relatively less rigid material as compared with that of the rest of the nasal joint tube.

14. The nasal cannula device of claim 2, wherein the nasal joint tube further comprises an aperture formed thereon.

15. The nasal cannula device of claim 2, further comprising a head gear having two supporters, which are coupled to the left and right ends of the base, respectively.

16. The nasal cannula device of claim 15, wherein the rear side of the cannula body further comprises two blocking tabs, in which each blocking tab is formed at each lateral end of the wing to help secure the head gear in place.

* * * * *